(12) United States Patent
Plachetka et al.

(10) Patent No.: US 7,332,183 B2
(45) Date of Patent: Feb. 19, 2008

(54) MULTILAYER DOSAGE FORMS CONTAINING NSAIDS AND TRIPTANS

(75) Inventors: John R. Plachetka, Chapel Hill, NC (US); Venkata Markandeya Kothapalli, Cary, NC (US); Donna L. Gilbert, Chapel Hill, NC (US)

(73) Assignee: Pozen Inc., Chapel Hill, NC (US)

( * ) Notice: Subject to any disclaimer, the term of this patent is extended or adjusted under 35 U.S.C. 154(b) by 650 days.

(21) Appl. No.: 10/741,592

(22) Filed: Dec. 22, 2003

(65) Prior Publication Data
US 2004/0180089 A1 Sep. 16, 2004

Related U.S. Application Data

(60) Provisional application No. 60/436,000, filed on Dec. 26, 2002.

(51) Int. Cl.
A61K 9/24 (2006.01)
(52) U.S. Cl. .................................. 424/472
(58) Field of Classification Search ............. 424/472, 424/473, 474
See application file for complete search history.

(56) References Cited

U.S. PATENT DOCUMENTS

| | | | | |
|---|---|---|---|---|
| 701,438 | A * | 6/1902 | Whyte ..................... | 424/464 |
| 2,951,792 | A * | 9/1960 | Swintosky ................. | 424/472 |
| 3,048,526 | A * | 8/1962 | Boswell .................... | 424/472 |
| 3,317,394 | A * | 5/1967 | Ostholm et al. ........... | 424/472 |
| 3,358,687 | A * | 12/1967 | Miley et al. ............... | 604/288 |
| 4,024,279 | A | 5/1977 | Zor et al. .................. | 424/319 |
| 4,786,500 | A * | 11/1988 | Wong ....................... | 424/422 |
| 4,814,181 | A * | 3/1989 | Jordan et al. .............. | 424/473 |
| 4,816,470 | A | 3/1989 | Dowle et al. .............. | 514/415 |
| 4,946,685 | A * | 8/1990 | Edgren et al. ............. | 424/472 |
| 5,307,845 | A | 5/1994 | Vanrobaeys et al. ....... | 139/1 R |
| 5,307,953 | A | 5/1994 | Regan ...................... | 222/82 |
| 5,360,925 | A | 11/1994 | Chabrier de Lassauniere et al. .................... | 560/169 |
| 5,387,604 | A | 2/1995 | McDonald et al. ........ | 514/456 |
| 5,425,950 | A * | 6/1995 | Dandiker et al. .......... | 424/480 |
| 5,474,995 | A | 12/1995 | Ducharme et al. ........ | 514/241 |
| 5,480,650 | A | 1/1996 | Marchi et al. ............. | 424/464 |
| 5,514,168 | A | 5/1996 | Friedman .................. | 607/89 |
| 5,554,639 | A | 9/1996 | Craig et al. ................ | 514/415 |
| 5,605,917 | A | 2/1997 | Ogletree ................... | 514/365 |
| 5,607,960 | A | 3/1997 | Wythes ..................... | 514/414 |
| 5,618,816 | A | 4/1997 | Crenshaw et al. ......... | 514/253 |
| 5,637,320 | A | 6/1997 | Bourke et al. ............. | 424/489 |
| 5,698,571 | A | 12/1997 | Audia et al. ............... | 514/323 |
| 5,705,520 | A | 1/1998 | Craig et al. ................ | 514/415 |
| 5,807,571 | A | 9/1998 | List .......................... | 424/449 |
| 5,872,145 | A | 2/1999 | Plachetka .................. | 514/415 |
| 5,942,503 | A | 8/1999 | Jung et al. ................. | 514/214 |
| 6,060,499 | A | 5/2000 | Plachetka .................. | 514/415 |
| 6,077,539 | A * | 6/2000 | Plachetka et al. .......... | 424/474 |
| 6,245,802 | B1 | 6/2001 | Iyengar et al. ............. | 514/438 |
| 6,365,184 | B1 | 4/2002 | Depui et al. ............... | 424/469 |
| 6,368,627 | B1 | 4/2002 | Phillips et al. ............. | 424/480 |
| 6,384,034 | B2 | 5/2002 | Simitchieva et al. ....... | 514/252 |
| 6,387,410 | B1 | 5/2002 | Woolfe et al. ............. | 424/489 |
| 6,635,281 | B2 * | 10/2003 | Wong et al. ............... | 424/473 |
| 6,797,283 | B1 * | 9/2004 | Edgren et al. ............. | 424/472 |
| 6,863,901 | B2 * | 3/2005 | Hirsh et al. ............... | 424/472 |
| 2002/0016348 | A1 | 2/2002 | Simitchieva et al. | |
| 2002/0099059 | A1 | 7/2002 | Saper .................... | 514/263.31 |
| 2003/0203027 | A1 * | 10/2003 | Verreck et al. ........... | 424/471 |
| 2003/0232876 | A1 | 12/2003 | Plachetka .................. | 514/419 |
| 2007/0184109 | A1 * | 8/2007 | Floyd et al. ............... | 424/465 |

FOREIGN PATENT DOCUMENTS

| | | |
|---|---|---|
| CS | 277 525 | 2/1993 |
| DE | 195 42 281 | 5/1997 |
| EP | 0 117 164 | 8/1984 |
| EP | 0 379 314 | 7/1990 |
| EP | 0 447 727 | 9/1991 |
| EP | 1 051 993 A2 | 11/2000 |
| EP | 1 051 995 A2 | 11/2000 |
| EP | 1 064 948 A2 | 1/2001 |
| EP | 1 064 966 A2 | 1/2001 |
| EP | 1 064 967 A2 | 1/2001 |
| EP | 1 126 841 | 12/2004 |
| GB | 2 124 210 | 2/1984 |
| GB | 2 135 884 | 9/1984 |
| GB | 2 162 522 | 2/1986 |
| JP | 8-208516 | 8/1996 |
| WO | WO 94/26270 | 11/1994 |

(Continued)

OTHER PUBLICATIONS

Certified Translation of EP 0 117 164, Reference B9 above.
Andersson, et al., "Double-Blind Study of Naproxen vs Placebo in the Treatment of Acute Migraine Attacks," *Cephalalgia* 9:29-32 (1989).
Baumel, "Migraine: A Pharmacologic Review with Newer Options and Delivery Modalities," *Neurology* 44:S13-S17 (1994).
Bolten, "Scientific Rationale for Specific Inhibition of COX-2," *J. Rheumatol.* 25:2-7 (1998).
Boureau, et al., "Comparison of Subcutaneous Sumatriptan with Usual Acute Treatments for Migraine," *Eur. Neurol.* 35:264-269 (1995).

(Continued)

*Primary Examiner*—Sharon Kennedy
(74) *Attorney, Agent, or Firm*—Michael A. Sanzo; Law Office of Michael A. Sanzo, LLC (57) ABSTRACT

The present invention is directed to multilayer pharmaceutical tablets in which an NSAID and a triptan are present in separate and distinct layers. The layers are in a side-by-side configuration, which allows the dissolution of triptan and NSAID to occur independently and immediately.

20 Claims, 1 Drawing Sheet

FOREIGN PATENT DOCUMENTS

| | | |
|---|---|---|
| WO | WO 97/38986 | 10/1997 |
| WO | WO 98/06392 | 2/1998 |
| WO | WO 98/15275 | 4/1998 |
| WO | WO 98/20870 | 5/1998 |
| WO | WO 99/45905 | 9/1999 |
| WO | WO 00/06161 | 2/2000 |
| WO | WO 00/25779 | 5/2000 |
| WO | WO 00/48583 | 8/2000 |

OTHER PUBLICATIONS

Bousser, et al., "Combined Low-Dose Acetylsalicyclic Acid and Dihydroergotamine in Migraine Prophylaxis," *Cephalalgia* 8:187-102 (1988).

Bousser, et al., "Efficacy of Subcutaneous Sumatriptan in the Acute Treatment of Early-Morning Migraine: A Placebo-Controlled Trial," *J. Intern. Med.* 234:211-216 (1993).

Cady, et al., "Treatment of Acute Migraine with Subcutaneous Sumatriptan," *JAMA* 265:2831-2835 (1991).

Cady, et al., "Efficacy of Subcutaneous Sumatriptan in Repeated Episodes of Migraine," *Neurology* 43:1363-1368 (1993).

Cady, et al., "Recent Advances in Migraine Management," *J. Family Practice* 36(1):85-91 (1993).

Capobianco, et al., "An Overview of the Diagnosis and Pharmacologic Treatment of Migraine," *Mayo Clin. Proc.* 71:1055-1066 (1996).

Centonze, et al., "Evaluation of the Efficacy of Oral Sumatriptan in the Management of Migraine Attacks. Clinical Results," *La Clinica Teraputica* 146:721-728 (1995). (Article in Italian with English Abstract).

Dahlöf, "How Does Sumatriptan Perform in Clinical Practice," *Caphalalgia* 15:21-28 (1995).

Dechant, et al., "Sumatriptan—A Review of Its Pharmacodynamic and Pharmacokinetic Properties, and Therapeutic Efficacy in the Acute Treatment of Migraine and Cluster Headache," *Drugs* 43:776-798 (1992).

Demarin, et al., "Pharmacotherapy of Migraine," *Acta Clin. Croat.* 34:81-89 (1995).

Donnelly, et al., "Review Article: COX-II Inhibitors—a New Generation of Safer NSAIDs?," *Aliment. Pharmacol. Ther.* 11:227-236 (1997).

Furlong, et al., "Prescribing Practices for the Management of Headache in Newfoundland and Labrador," *Headache* 36:542-546 (1996).

Furst, "Meloxicam: Selective COX-2 Inhibition in Clinical Practice," *Semin. Arthritis Rheum.* 26:21-27 (1997).

Grazzi, et al., "A Review of the Treatment of Primary Headaches. Part I: Migraine," *Intl. J. Neurol. Sci.* 16:577-586 (1995).

Griswold, et al., "Constitutive Cyclooxygenase (COX-1) and Inducible Cyclooxygenase (COX-2): Rationale for Selective Inhibition and Progress to Date," *Med. Res. Rev.* 16:181-206 (1996).

Haag, "Kombianalgetika in der Kopfschemerz-therapie," *Duetsche Apotheker Zeitung, De, Deutscher Apotheker Zeitung* 4:43-48 (1993) Stuttgart.

Hoernecke, et al., "Treatment of Migraine Attacks: Combination of Dihydroergotamine Tartrate and Paracetamol in Comparison with Individual Drugs and Placebo," *Medizinische Klinik* 88:642-648 (1993); Abstract from Medline Online, Database Accession No. NLM8295604.

Klapper, "The Pharmacologic Treatment of Acute Migraine Headaches," *J. Pain Symptom Manage.* 8:140-147 (1993).

Klapper, "Toward a Standard Drug Formulary for the Treatment of Headache," *Headache* 35:225-227 (1995).

Kumar, "Recent Advances in the Acute Management of Migraine and Cluster Headaches," *J. Gen. Internal Med.* 9:339-348 (1994).

Krymchantowski, et al., "Tolfenamic Acid Decreases Migraine Recurrence When Used with Sumatriptan," *Cephalalgia* 19:186-187 (1999).

Krymchantowski, et al., "Naproxen Sodium Decreases Migraine Recurrence When Used with Sumatriptan," *Cephalalgia* 19:357-358 (1999).

Lance, "Headache," *Ann. Neurol.* 10:1-10 (1981).

Lane, "Pain Management in Osteoarthritis: The Role of COX-2 Inhibitors," *J. Rheumatol.* 24:20-24 (1997).

Lipsky, et al., "Outcome of Specific COX-2 Inhibition in Rheumatoid Arthritis," *J. Rheumatol.* 24:9-14 (1997).

Mathew, "Cyclical Prophylactic Treatment of Menstrual Migraine Using Naproxen and Ergotamine," *Headache* 26:314 (1986).

Mathew, et al., "Advances in Migraine Drug Therapy," *Drug Therapy* 23:37-48 (1993).

Moskowitz, et al., "Neuroeffector Functions of Sensory Fibres: Implications for Headache Mechanisms and Drug Actions," *J. Neurol.* 238:S-18-S22 (1991).

Myllylä, et al., "Tolfenamic Acid Rapid Release Versus Sumatriptan in the Acute Treatment of Migraine: Comparable Effect in a Double-Blind, Randomized, Controlled, Parallel-Group Study," *Headache* 38:201-207 (1998).

Oral Sumatriptan Group, "Sumatriptan—An Oral Dose-Defining Study," *Eur. Neurol.* 31:300-305 (1991).

Parma, et al., "Il Trattamento dell'Emicrania: Uno Studio Nella Medicina Generale," *Ricerca & Pratica* 11:64-72 (1995) in Italian. Translation of AK5 above: Parma, et al., "The Treatment of Migraine: A Study in General Medicine," *Ricerca & Pratica* 11:64-72 (1995).

Peroutka, "Beyond Monotherapy: Rational Polytherapy in Migraine," *Headache* 38:18-22 (1998).

Pfaffenrath, et al., "Efficacy and Safety of Sumatriptan Tablets (25 mg, 50 mg, and 100 mg) in the Acute Treatment of Migraine: Defining the Optimum Doses of Oral Sumatriptan," *Headache* 38:184-190 (1998).

Plosker, et al., "Sumatriptan: A Reappraisal of Its Pharmacology and Therapeutic Efficacy in the Acute Treatment of Migraine and Cluster Headache," *Drugs* 47:622-651 (1994).

Pradalier, et al., "La Migraine Cataméniale," *Contracept. Fertil. Sex.* 23:361-365 (1995) in French.

Translation of AP5 above: Pradalier, et al., "Menstrual Migraine," *Contracept. Fertil. Sex.* 23:361-365 (1995).

Prusinski, "Monotherapy or Polytherapy in Migraine", *Neuroepidemiology* 6:186-189 (1987).

Rac, et al., "Formulation of Antimigraine Mixtures," STN HCA, vol. 8 (1994), abstract—XP-002078672.

Saadah, "Abortive Migraine Therapy with Oral Naproxen Sodium Plus Metoclopramide Plus Ergotamine Tartrate with Caffeine," *Headache* 32:95-97 (1992).

Schuller, et al., "Recurrent Headaches: What Every Allergist Should Know," *Ann. Allergy Asthma Immunol.* 76:219-230 (1996).

Sharma, et al., "An Update on Eicosanoids and Inhibitors of Cyclooxygenase Enzyme Systems," *Indian J. Exper. Biol.* 35:1025-1031 (1997).

Sheftell, et al., "Subcutaneous Sumatriptan in a Clinical Setting: The First 100 Consecutive Patients with Acute Migraine in a Tertiary Care Center," *Headache* 34:67-72 (1994).

Silberstein, "Treatment of the Migraine Attack," *Curr. Opn. Neurol.* 7:258-263 (1994).

Solomon, "Therapeutic Advances in Migraine," *J. Clin. Pharmacol.* 33:200-209 (1993).

Thomson, "A Study to Compare Oral Sumatriptan with Oral Aspirin plus Oral Metoclopramide in the Acute Treatment of Migraine," *Eur. Neurol.* 32:177-184 (1992).

Todd, et al., "Naproxen: A Reappraisal of Its Pharmacology, and Therapeutic Use in Rheumatic Diseases and Pain States," *Drugs* 40:91-137 (1990).

Tokola, et al., "Effects of Migraine Attack and Metoclopramide on the Absorption of Tolfenamic Acid," *Br. J. Clin. Pharmac.* 17:67-75 (1984).

Tokola, et al., "Tolfenamic Acid, Metroclopramide, Caffeine and their Combinations in the Treament of Migraine Attacks," *Cephalalgia* 4:253-263 (1984).

Von Seggern, et al., "Cost Considerations in Headache Treatment Part 2: Acute Migraine Treatment," *Headache* 36:493-502 (1996).

Welch, "Drug Therapy of Migraine," *N. E. J. Med.* 329:1476-1483 (1993).

Wilkinson, et al., "Migraine Cluster Headache—their Management with Sumatriptan: A Critical Review of the Current Clinical Experience," *Cephalalgia 15*:337-357 (1995).

Witting, "Renal Papillary Necrosis Following Emergency Department Treatment of Migraine," *J. Emer. Med.* 14:373-376 (1996).

Abstracts of Talley, et al., O.D. Searle Celebrix Registry 169590-42-5, "Celebrex," SC58635, patients for migraine headache: 5,466,823 (Nov. 1995); 5,504,215 (Apr. 1996); 5,508,426 (Apr. 1996); 5,510,496 (Apr. 1996); 5,516,907 (May 1996); 5/521,207 (May 1996); 5,563,165 (Oct. 1996); 5,700,816 (Dec. 1997); 5,753,688 (May 1998); 5,760,068 (Jun. 1998); and 5,932,598 (Aug. 1999).

English language abstract of WO 94/26270, Reference B1 above.

English language abstract of DE 195 42 281, Reference B16 above.

English language abstract of JP 8-208516, Reference B7 above.

Buzzi, et al., "Evidence for 5-HT1B/1D Receptors Mediating the Antimigraine Effect of Sumatriptan and Dihydroergotamine," *Cephalalgia 11*:165-168 (1991).

Sternfeld, et al., "The Chemical Evolution of N,N-Dimethyl-2-[5-(1,2,4-Triazol-4-YL)-1H-Indol-3-YL]Ethylamine (L-741,604) and Analogues: Potent and Selective Agonists for 5-HT$_{1D}$ Receptors," *Biorganic and Medicinal Chemistry Letters 6*(15):1825-1830 (1996).

Extract from *The Pharmacological Basis of Therapeutics*, Goodman & Gilman, 9th Ed.

*The Merck Index*, 12th Ed., 1996: THER-12-13.

*The Merck Index*, 13th Ed., 2001:1480.

*Physicians' Desk Reference*,® 50th Ed., 1996, Imitrex® : 1106-1110.

*Physicians' Desk Reference*,® 50th Ed., 1996, Naproxen® :2110-2113.

Search results obtained from the "Integrity" and "Pharmaprojects" databases, following a query for "ALX-1323."

Test Report prepared by Opponent Almirall Prodesfarma SA.

Opposition papers filed by Opponent Almirall Prodesfarma SA.

Opposition papers filed by Opponent Merck & Co., Inc.

English language translation for CS 277 525, Reference B1 above.

Brandes, et al., "Superior Efficacy of Combination Therapy over Monotherapy: Results of a Fixed Single-Tablet Formulation of Sumatriptan RT Technology and Naproxen Sodium in the Acute Treatment of Migraine in the Traditional Treatment Paradigm," Abstract (accepted for presentation), 48th Annual Specific Meeting of the American Headache Society, Jun. 22-26, Los Angeles, CA.

Brandes, et al. "Therapeutic Clinical Benefits of a New Single-Tablet Formulation of Sumatriptan Formulated with RT Technology™ and Naproxen Sodium," *Cephalalgia 25*:860 (2005).

Dahlöf, "Infrequent or Non-Response to Oral Sumatriptan Does Not Predict Response to Other Triptans—Review of Four Trials," *Cephalalgia 26*:98-106 (2005).

Ferrari, et al., "Triptans (serotonin, 5-HT$_{1B/1D}$ Agonists) in Migraine: Detailed Results and Methods of a Meta-Analysis of 53 Trials," *Cephalalgia 22*:633-658 (2002).

Fowler, et al., "The Effect of Anti-Prostaglandins and Anti-Histamines on the Tolerability Profile of Sumatriptan," *New Adv. Headache Res.* 4:318 (1994).

Fuseau, et al., "Effect of Encapsulation on Absorption of Sumatriptan Tablets: Data from Healthy Volunteers and Patients During a Migraine," *Clin. Therapeutics 23*:242-251 (2001).

Krymchantowski, et al., "Rizatriptan Versus Rizatriptan Plus Rofecoxib Versus Rizatriptan Plus Tolfenamic Acid in the Acute Treatment of Migraine," *BMC Neurology 4*:10 (2004).

Krymchantowski, "Naproxen Sodium Decreases Migraine Recurrence When Administered with Sumatriptan," *Arq Neuropsiquiatr 58*(2-B):428-430 (2000).

Krymchantowski, et al., "Rizatriptan Combined with Rofecoxib vs. Rizatriptan for the Acute Treatment of Migraine: An Open Label Pilot Study," *Cephalalgia 22*:309-312 (2002).

Louis, et al., "Crossover and Self-Controlled Designs in Clinical Research," *N. Engl. J. Med.* 310:24-31 (1984).

Mandema, et al., "Therapeutic Benefit of Eletriptan Compared to Sumatriptan for the Acute Relief of a Migraine Pain—Results of a Model-Based Meta-Analysis that Accounts for Encapsulation," *Cephalalgia 25*:715-725 (2005).

Silberstein, et al., "Superior Clinical Benefits of a New Single-Tablet Formulation of Sumatriptan Formulated with RT Technology and Naproxen Sodium," Abstract S35.001, 58th Annual Meeting of the American Academy of Neurology, presented Apr. 5, 2006, San Diego, CA.

Smith, et al., "Sumatriptan and Naproxen Sodium for the Acute Treatment of Migraine," *Headache 45*:983-991 (2005).

Spierings, "Eletriptan in Acute Migraine: A Double-Blind, Placebo-Controlled Comparison to Sumatriptan," *Neurology 55*:735-742 (2000).

Visser, et al., "Risk Factors for Headache Recurrence after Sumatriptan: A Study in 366 Migraine Patients," *Cephalalgia 16*:264-269 (1996).

Various Letters to the Editor, *Headache* 921-929 (Sep. 2003).

Extract from *The Pharmacological Basis of Therapeutics*, Goodman & Gilman, 9th Ed., pp. 231 and 491-498.

Response filed in European Oppositions of Merck and Almirall.

Comparison of Chemical Structures of Ergots and Triptans, *Modern Drug Discovery*, vol. 2 (1999).

European Search Report for Application Number EP03808537.9.

\* cited by examiner

Figure 1.

Representative drawings of three different dosage form configurations.

Panel A: Multi-Layer Tablet (Bilayer Tablet Shown)

Panel B: Naproxen Sodium Core Tablet with Sumatriptan Succinate in the Film-Coat Panel C: Physical Admixture

US 7,332,183 B2

MULTILAYER DOSAGE FORMS CONTAINING NSAIDS AND TRIPTANS

CROSS REFERENCE TO RELATED APPLICATIONS

This application claims priority to U.S. provisional application No. 60/436,000, filed on Dec. 26, 2002, which is incorporated in its entirety herein by reference.

FIELD OF THE INVENTION

The present invention is in the general field of treatments for pain, and particularly treatments for pain associated with migraine headache. It encompasses solid dosage forms having triptans and NSAIDs, particularly naproxen, in a multilayer arrangement. In addition, the invention is concerned with methods of treating headache using these dosage forms.

BACKGROUND OF THE INVENTION

It has been estimated that 6% of men and 18% of women in the United States currently suffer from migraine headaches. Often, patients experience 30 or more potentially debilitating attacks a year. Current treatments include a range of over-the-counter analgesics as well as ergotamines and triptans.

Recently, reports have indicated that combination therapies in which triptans are combined with NSAIDs greatly improve the relief available to migraine patients (U.S. Pat. No. 6,060,499; U.S. Pat. No. 5,872,145; see also U.S. Pat. No. 6,384,034; U.S. 2002/0099059; EP 1051993; EP 1064967; EP 1051995; EP 10649966; and EP 1064948). In general, NSAIDs have been delivered orally, for example in the form of either single or multilayer tablets or as coated granules (U.S. Pat. No. 6,365,184; U.S. Pat. No. 5,637,320; U.S. Pat. No. 5,480,650; and U.S. Pat. No. 6,387,410). Triptans have been given orally, intranasally and by injection (see, e.g., U.S. Pat. No. 4,816,470; U.S. Pat. No. 5,307,845; U.S. Pat. No. 5,307,953; U.S. Pat. No. 5,554,639; and U.S. Pat. No. 5,705,520; U.S. Pat. No. 6,368,627; and WO 00/06161).

Although a good deal of work has been done in the area of dosage forms for triptans and NSAIDs, relatively little is known about the properties of dosage forms. in which these agents are combined. The way in which such dosage forms are constructed may affect not only the stability of the individual therapeutic agents but also the speed at which the individual agents dissolve and become available to provide pain relief to patients.

SUMMARY OF THE INVENTION

The present invention is directed to specific oral dosage forms containing a triptan and an NSAID, especially naproxen, in which these therapeutic agents are segregated into separate layers of a multilayer tablet. Unless otherwise specified, reference to an NSAID or a triptan will be understood to include pharmaceutically acceptable salts of these drugs. The dosage forms of the invention have been found to have substantial advantages over others in terms of release properties, stability and pharmacokinetic profile. These advantages could not have been predicted a priori and make the dosage forms the selection of choice for the treatment of patients with migraine headache.

In its first aspect, the invention is directed to a multilayer pharmaceutical tablet comprising naproxen (preferably naproxen sodium at a therapeutic dosage of between 200 and 600 mg) and a triptan. Most preferably, the tablet has 40 mg of sodium succinate, 400 mg naproxen sodium and may be formulated as described in Example 6B. Substantially all of the triptan is found in one layer of the tablet and substantially all of the naproxen is found in a second, separate layer. These two layers are in a side-by-side arrangement such that the dissolution of the naproxen occurs independently of the dissolution of triptan. As discussed further below, this tablet arrangement has surprisingly better properties than other tablet arrangements. Without being held to any particular theory, it is believed that, in the stomach, naproxen forms a gel-like matrix that retards the dissolution of triptans (or other drugs) unless the two agents are maintained in distinct, side by side layers.

Other types of NSAIDs whose characteristics might possibly be improved by a side by side tablet configuration include acidic NSAIDs, i.e., NSAIDs having a $pK_a$ of less than 7.0, and, long acting NSAIDs, i.e., NSAIDs having a half life of at least four hours and duration of action of at least six hours. Examples of long acting NSAIDs that might be used include flurbiprofen, ketoprofen, naproxen, oxaprozin, etodolac, indomethacin, ketorolac, nabumetone, mefanamic acid, piroxicam, lornoxicam, meloxicam, and pharmaceutically acceptable salts thereof. Another group of NSAIDs that could be used is the cyclooxygenase-2 (COX-2) inhibitors. Members of this group include: rofecoxib; celecoxib, valdecoxib, etoricoxib, JTE-522; L-745,337; NS398; and pharmaceutically acceptable salts thereof. The most preferred of these is rofecoxib which has a half life of about 17 hours. Preferably this should be present in tablets in an amount of between 10 and 50 mg and the total initial daily dose should not exceed 50 mg.

Examples of triptans that may be used include sumatriptan, eletriptan, rizatriptan, frovatriptan, almotriptan, zolmitriptan, and naratriptan and pharmaceutically acceptable salts thereof. The most preferred of these is sumatriptan at a therapeutic dose of between 25 and 100 mg. The other triptans should be administered to patients at the dosages known in the art to be effective at relieving pain.

As discussed above, substantially all of the triptan and substantially all of the NSAID in dosage forms should be in separate layers. The term "substantially all" indicates that at least 90%, and preferably greater than 95%, of the total therapeutic agent present in the tablet is included within one distinct layer. The layers should be arranged such that the individual therapeutic agents dissolve independently of one another, i.e., dissolution should occur at approximately the same rate as would occur if the drugs were given separately. In this context, "approximately the same rate" indicates that the time for complete dissolution of agent when drugs are given in the combination tablet should require the same amount of time±10% as when the same amount of agent is given alone. This can be achieved by placing the individual layers in a side-by-side arrangement, as opposed, for example, in a single layer tablet matrix containing both agents or one layer forming a core surrounded by the other layer. In a preferred embodiment, the layers are arranged so that they are juxtaposed symmetrically along a single planar surface such that essentially all of the triptan-containing layer is on one side of the plane and essentially all of the NSAID-containing layer is on the other side. The term "essentially all" is equivalent to "substantially all" and means that at least 90% and preferably greater than 95% of the therapeutic agent is present. These layers may come into direct contact with one another or, alternatively, they may be separated by one or more additional layers, e.g., a barrier layer or coating which prevents the therapeutic agents from interacting with one another. In preferred embodiments, the tablets are in a bilayer arrangement and may be surrounded with a film coating.

In an alternative aspect, the invention is directed to methods of treating a patient for headache, preferably migraine headache, by administering any of the tablets described above. Other types of headache that can be treated include tension-type headache; cluster headache and chronic paroxysmal hemicrania; miscellaneous headache unassociated with a structural lesion; headache associated with a non-vascular intracranial disorder; headache associated with the administration of a substance or its withdrawal; headache associated with noncephalic infection; headache associated with a metabolic disorder; headache associated with a disorder of the cranium, neck, eyes, ears, nose, sinuses, teeth, mouth or other facial or cranial structure; cranial neuralgias; and nerve trunk pain and deafferentiation pain. (For a description of headache classes, see Olesen, et al., *The Headaches*, pp. 9-14, Raven Press; see also, "Classification and diagnostic criteria for headache disorders, cranial neuralgias and facial pain," Headache Classification Committee of the International Headache Society, *Cephalalgia* 8(*supp.* 7):1-96 (1988)). In all cases, sufficient analgesic should be administered to alleviate the pain associated with the condition being treated.

BRIEF DESCRIPTION OF THE DRAWINGS

FIG. 1.

DETAILED DESCRIPTION OF THE INVENTION

The present invention is directed to certain specific oral dosage forms which contain both a triptan and an NSAID, preferably naproxen. The main characteristics of the dosage forms are that they are in the form of tablets in which the triptan and NSAID are maintained in separate distinct layers and dissolve in an independent manner. Experiments discussed in the Examples section have shown that, in other types of tablets, the dissolution of triptan is delayed. Applicants believe that naproxen and similar NSAIDs possess poor solubility in vivo due, in part, to the stomach's low pH environment. This poor solubility may impart slower drug release properties for a given dosage form. Because of the slow eroding nature of naproxen sodium tablets and similar NSAIDs, triptans may become entrapped, and, as a result, their release may be delayed when non-segregated tablets are used. By maintaining the triptan and NSAID in separate layers, this problem is avoided. Thus, a multilayer or bilayer tablet provides for independent and immediate release of each component and has favorable biopharmaceutical attributes with respect to headache pain relief. In addition, experiments have shown that physiochemical stability is improved when NSAID and triptan are maintained in distinct layers.

Any method for producing multilayered tablets is compatible with the present invention with the only restriction being that the triptan and NSAID must be separated. Preferred methods for producing tablets are described in the Examples section. If an NSAID other than naproxen is used, then it is desirable that it be a long-acting NSAID because of the longer duration of pain relief resulting from these agents. Naproxen and naproxen sodium are themselves long acting NSAIDs with half lives of about 12 to 15 hours and about 12 to 13 hours, respectively. Examples of other long acting NSAIDs include flurbiprofen, with a half life of about 6 hours; ketoprofen, with a half life of about 4 hours; oxaprozin, with a half life of about 42 to 50 hours; etodolac, with a half life of about 7 hours; indomethacin, with a half life of about 4 to 6 hours; ketorolac, with a half life of about 8 to 9 hours; nabumetone, with a half life of about 22 to 30 hours; mefanamic acid, with a half life of about 4 hours; and piroxicam, with a half life of about 4 to 6 hours. Any salt form of NSAID or triptan is compatible with the invention.

Any of the triptans that have been reported in the literature may also be used in the present invention. Sumatriptan is the most preferred and should be administered to patients at a dosage of between 1 and 300 mg with dosages of 25-100 mg being preferred. Effective dosages for a variety of NSAIDs are: indomethacin—three 25 mg doses taken at intervals during the day, 75 mg total; flurbiprofen—tablets of 50-100 mg with a total daily dosage of between 100 and 500 mg and preferably between 200 and 300 mg; ketoprofen—tablets of 25-75 mg with a total daily dosage of 100-500 mg and preferably 100-300 mg; naproxen—tablets of 250-500 mg and, for the sodium salt, tablets of 275-550 mg; oxaprozin—tablets of about 600 mg with a total daily dose of about 1200 mg; etodolac—tablets of about 400 mg with a total daily dosage of less than 1200 mg; ketorolac—tablets of 10-40 mg; nabumetone—tablets of 500-750 mg with a total daily dosage of 1500-2000 mg; mefanamic acid—tablets containing 100-1000 mg with about 500 mg being typical; and piroxicam—tablets of 10-20 mg. This information concerning tablets and dosages are provided merely as guidelines and it is expected that one of ordinary skill in the art would make certain adjustments either for convenience or to better suit the needs of particular patients.

The compositions described herein can be made in accordance with methods that are standard in the art (see, e.g., *Remington's Pharmaceutical Sciences*, 16$^{th}$ ed., A. Oslo Editor, Easton, Pa. (1980)). In addition to the active agents, the different layers of tablets may contain binders (e.g., polyvinylpyrrolidone), disintegrants (e.g., microcrystalline cellulose, or croscarmellose sodium), lubricants (e.g., talc, or magnesium stearate) and fillers (e.g., lactose). The tablets may be coated or there may be a barrier or coating layer between layers containing active agents. Typical coating components that may be used include a polymer (e.g., hydroxypropylmethyl cellulose), a plasticizer (e.g., polyethylene glycol or polysorbate 80) and a coloring agent (e.g., titanium dioxide). A preferred formulation for the triptan layer of a tablet is shown in Table 1 below and a preferred formulation for the NSAID layer is shown in Table 2. Any standard manufacturing method for producing tablets using either a wet or dry granulation procedure is compatible with the invention and specific preferred methods are set forth in the Examples section below.

EXAMPLES

Example 1

Making of Bilayer Tablets and Other Dosage Forms

Figure 1:
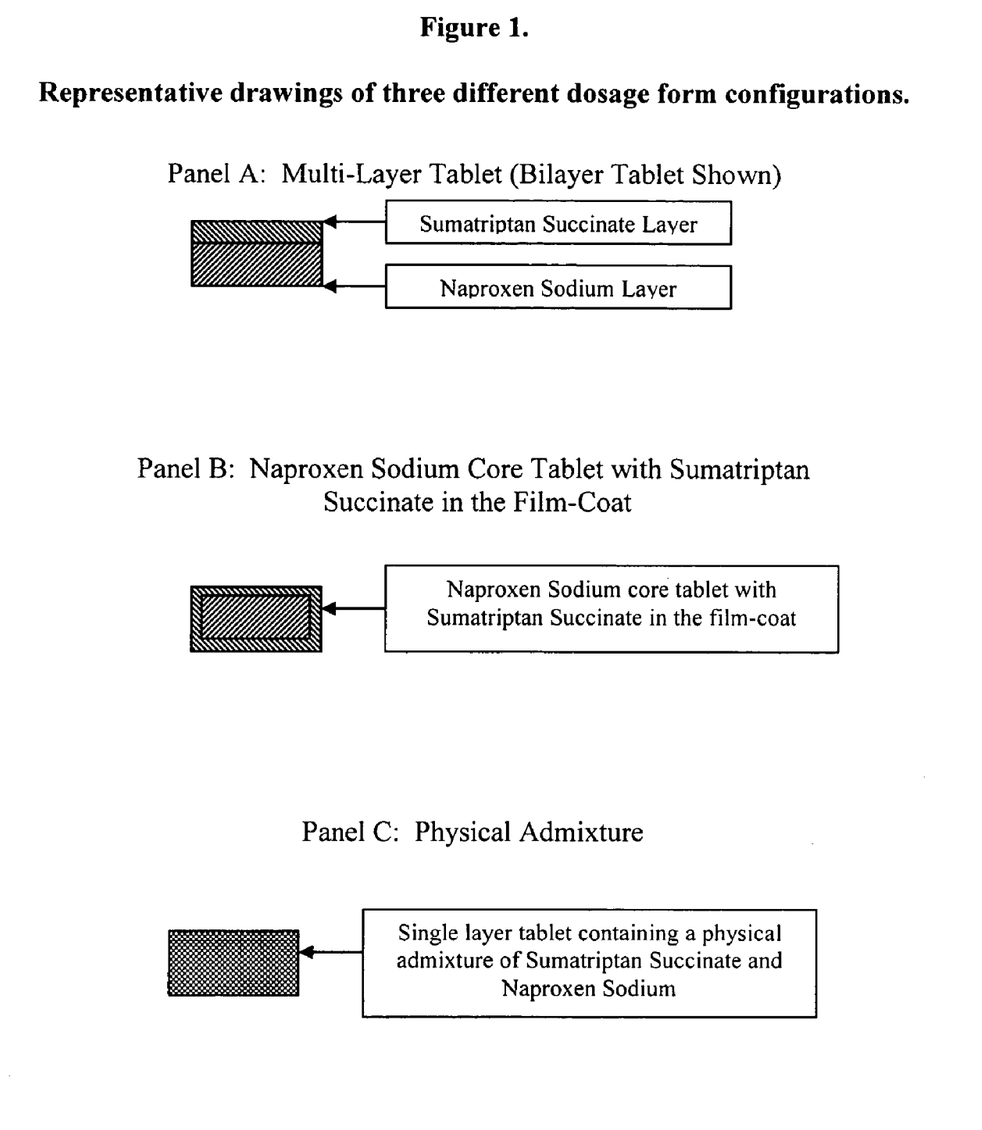
FIG. 1 depicts three different configurations that may be used for a tablet containing sumatriptan succinate and naproxen sodium. Panel A shows a side-by-side type configuration encompassed by the present invention. Panel B shows an arrangement in which naproxen sodium is present as a core surrounded by a coating of sumatriptan succinate, and panel C shows a single layer tablet in which there is an admixture of sumatriptan succinate and naproxen sodium.

The dosage forms of this invention can be prepared by different manufacturing processes. The manufacture of a bilayer tablet dosage form comprising sumatriptan succinate and naproxen sodium layers with acceptable carriers is described below in subsection A and large scale methods of manufacturing these tablets are described in Example 5. In brief, the manufacturing process for the separate granulations incorporates high shear granulation, fluid-bed drying, milling, blending, and lubrication. The production of alternative dosage forms (naproxen sodium core tablets with sumatriptan succinate in the film-coat or a physical admixture of naproxen sodium and sumatriptan succinate granulations) is described in subsections B and C. Representative drawings of the dosage forms are shown in FIG. 1.

A. Bilayer Tablet Dosage Form

The present invention is directed to pharmaceutical compositions comprising tablets in which sumatriptan succinate and naproxen sodium are present in distinct layers together with acceptable carriers (APhA, *In Handbook of Pharmaceutical Excipients*; Wade et al., eds, The Pharmaceutical Press, Washington, 1994). The manufacture of tablets is described below and involves the application of standard methods well known in the art of pharmaceutical sciences (Rubinstein, M. H. In *Pharmaceutics: The Science of Dosage Form Design*; Bandelin, In *Pharmaceutical Dosage Forms: Tablets*, Lieberman, et al. eds., Marcel Dekker, Inc., New York, 1989, p. 131-193; and Carstensen, J. T. In *Pharmaceutics of Solids and Solid Dosage Forms*, John Wiley & Sons: New York, 1977). The separate processes for each granulation incorporate high shear granulation, fluidbed drying, milling, blending, and lubrication. The formulation composition for each separate granulation is provided in Tables 1 and 2. The dose ratios of the components may be varied within the therapeutic ranges.

Manufacturing Steps

1. Separately charge the respective intra-granular ingredients from Tables 1 (sumatriptan succinate) and 2 (naproxen sodium) into suitable high shear mixer/granulators (Niro/Fielder, GP-1 or PMA-65).
2. Dry mix for 5 minutes using a high impeller speed and a high chopper speed setting. Using a spray gun/nozzle, spray purified water, USP, granulating solution, at a controlled rate, while mixing continuously at the same mixing conditions. Continue to mix under the same conditions for one to three minutes or until proper granulation endpoint is reached. Record the final granulating time (solution addition and post-solution addition), amount of solution added, and mixer power consumption readings.
3. Remove the wet granules from the high shear mixer/granulator and place in a drying bowl and dry in a suitable fluid bed dryer (Niro, MP2/3), using the following conditions to achieve a loss on drying of 1-5%:
   a) inlet air temperature: 25-60° C.
   b) outlet air temperature: 35-55° C.
4. Sample the granulation to determine the moisture content.
5. Mill the dried granulation into a hopper or drum using a suitable mill (Quadro Comil, Model 197S) fitted with a suitable screen (0.094R) and operating at 2,500 rpm.
6. Charge the milled granulation and the respective extra-granular ingredients in Tables 1 and 2 into suitable V-blenders (Patterson-Kelly) or tote blenders (Gallay).
7. Blend for 10 minutes or until uniform.
8. Add lubricants, magnesium stearate and/or talc, through a # 40 mesh screen and blend for five minutes.
9. Transfer the separate final blends into double-line polyethylene bags.
10. Weigh the respective quantities of each blend using an analytical balance.
11. Manually compress the respective granulations as bilayer tablets using 7/16" standard concave, round shaped tooling and dies using a laboratory tablet press (Carver, Model C). Load the first layer, naproxen sodium blend, into the die first and tamp to remove entrapped air. Load the second layer, sumatriptan succinate blend, on top of the naproxen sodium layer and compress using 2,000 lbs force. Target a bilayer tablet hardness range of 8 to 14 kp.
12. In-process controls to ensure acceptable bilayer dosage form include respective weights of each layer, hardness (8-14 kp), thickness, friability (<1%), and disintegration (<15 minutes).
13. A barrier layer, consisting of 80:20 mixture of anhydrous lactose, NF and microcrystalline cellulose, NF, may be included between the naproxen sodium and sumatriptan succinate layers.

TABLE 1

Formulation Composition for Sumatriptan 35 mg Granulation[1]

| Ingredient | mg/Tablet |
| --- | --- |
| Intra-Granular Ingredients: | |
| Sumatriptan Succinate | 49.00 |
| Lactose Monohydrate, NF | 49.00 |
| Purified Water, USP[2] | QS |
| Extra-Granular Ingredients: | |
| Anhydrous Lactose, NF | 98.00 |
| Microcrystalline Cellulose, NF | 10.85 |
| Croscarmellose Sodium, NF | 2.10 |
| Magnesium Stearate, NF | 1.05 |
| Total | 210.00 |

[1]Free base equivalent. Representative formulation shown above; quantities of excipients may be varied by ± 10% to improve pharmaceutical processing efficiencies.
[2]Purified Water, USP is removed during the drying process.

TABLE 2

Formulation composition for Naproxen Sodium 375 mg granulation[1]

| Ingredient | mg/Tablet |
| --- | --- |
| Intra-Granular Ingredients: | |
| Naproxen Sodium, USP | 375.00 |
| Microcrystalline Cellulose, NF | 39.71 |
| Povidone, USP | 17.70 |
| Purified Water, USP[2] | QS |
| Extra-Granular Ingredients: | |
| Microcrystalline Cellulose, NF | 39.71 |
| Croscarmellose Sodium, NF | 10.12 |

TABLE 2-continued

| Formulation composition for Naproxen Sodium 375 mg granulation[1] | |
|---|---|
| Ingredient | mg/Tablet |
| Talc, USP | 20.25 |
| Magnesium Stearate, NF | 3.75 |
| Total | 506.24 |

[1]Representative formulation shown above; quantities of excipients may be varied by ± 10% to improve pharmaceutical processing efficiencies. Tablet weight may be adjusted for granulation moisture content.
[2]Purified Water, USP is removed during the drying process.

B. Naproxen Sodium Core Tablet with Sumatriptan Succinate in Film-coat

The manufacture of a dosage form in which a naproxen sodium core tablet is coated with a film comprising sumatriptan succinate is described below. The dose ratios of the components may be varied within the therapeutic ranges. Tablets may be made either without, or with, a barrier film-coat. The manufacturing process for naproxen sodium granulation incorporates high shear granulation, fluid-bed drying, milling, blending, lubrication, and compression, as described elsewhere (subsection A). The formulation composition for the naproxen sodium granulation is provided in Table 2.

The lubricated naproxen sodium granulation is compressed as a single layer tablet on a rotary tablet press (Korsch, Model PH-103) using 7/16" standard concave, round tooling and dies. Sufficient compression force (~3,800 lbs) is applied to yield acceptable conventional single layer tablets (weight~506.24 mg/tablet) with desired mechanical properties. The rotary tablet press speed is approximately 20 rpm. A tablet hardness of 8 to 14 kp and friability of less than 1% are targeted. To ensure acceptable core tablets, in-process controls include tablet weights, hardness, thickness, friability, and disintegration.

Approximately 28 g of sumatriptan succinate are dissolved in 305 g of purified water, USP and mixed until a clear solution is obtained. Approximately 18 g of Opadry® Clear (Formula # YS-1-19025A, Colorcon, Inc.) are added to the sumatriptan succinate solution and mixed until uniform. A coating insert is installed on a column coater (Niro, Model Strea) prior to charging the naproxen sodium core tablets. The core tablets are preheated for approximately 2 minutes with an inlet temperature of ~70° C. and then removed for a weight check. A 0.5 mm spray tip is installed on the spray gun and the core naproxen sodium tablets are coated to achieve a ~15% weight gain or 35 mg sumatriptan. During this process, the air flap is adjusted as necessary to maintain tablet fluidization. Similarly, the inlet temperature is adjusted as necessary to maintain the product bed temperature of ~40° C. and tablet weight gain is periodically checked. Once the target weight gain is obtained, the pump is stopped and the tablets are fluidized for approximately 5 minutes to dry the film-coat. An optional film-coat with colorants may be subsequently applied to enhance aesthetic attributes. The finished tablets are stored in double-lined polyethylene bags prior to packaging.

A variation of this dosage form incorporates application of a barrier film-coat layer consisting of Opadry® Clear onto the naproxen sodium core tablets. The clear-coated naproxen sodium tablets are then coated with the sumatriptan succinate/Opadry® Clear solution as before. An optional film-coat with colorants may be subsequently applied to enhance aesthetic attributes. The finished tablets are stored in double-lined polyethylene bags prior to packaging.

C. Physical Admixture of Naproxen Sodium and Sumatriptan Succinate

A pharmaceutical composition comprising a physical admixture of naproxen sodium and sumatriptan succinate granulations, is described below. The manufacturing process for the separate granulations incorporates high shear granulation, fluid-bed drying, and milling, as described above. The components of each granulation are shown in Tables 1 and 2, and the dose ratios may be varied within therapeutic ranges. Experiments were performed using sumatriptan succinate at various doses (25, 35, and 50 mg free base equivalent) and at a fixed dose of naproxen sodium (375 mg).

In order to manufacture the composition, appropriate amounts of the milled granulations are physically blended with extra-granular components, microcrystalline cellulose, NF and croscarmellose sodium, NF, in a suitable V-Blender for approximately 10 minutes. Pre-screened lubricants, talc, NF and magnesium stearate, NF, are added to the blend and mixed for approximately 5 minutes. The lubricated granulation is transferred to double-lined polyethylene bags prior to compression.

The granulation is compressed as a single layer on rotary tablet press (Korsch, Model PH-103) using 7/16" standard concave, round tooling and dies. Sufficient compression force (~3,800 lbs) is applied to yield acceptable conventional single layer tablets (weight 612.5 mg/tablet for the 25 mg sumatriptan as free base, 375 mg naproxen sodium dose composition) with desired mechanical properties. The rotary tablet press speed is approximately 20 rpm. A tablet hardness of 8 to 14 kp and friability of less than 1% are targeted. To ensure acceptable tablets, in-process controls include tablet weights, hardness, thickness, friability, and disintegration.

An optional film-coat may be applied to the tablets to enhance aesthetic attributes. The core tablets are film-coated in a perforated pan-coater (24" Accela-Cota), using a pre-mixed hydroxypropyl methylcellulose (HPMC) polymer-based dispersion with colorants (Opadry®, Colorcon, Inc.). A 12% w/w aqueous coating suspension is typically prepared. The tablets are coated using two spray guns with an inlet temperature of ~60° C. and an outlet temperature of ~40° C. The pan speed may range from 8-16 rpm. The finished tablets are stored in double-lined polyethylene bags prior to packaging.

A variation of this dosage form incorporates co-granulation of naproxen sodium and sumatriptan succinate with intra-granular components. Following wet granulation, the material is processed as described above to manufacture conventional single layer tablets.

Example 2

Dissolution Characteristics and Stability of Tablets

A. Analytical Methods

The utility of this invention is demonstrated by the improved dissolution and stability profile of bilayer tablet dosage form consisting of naproxen sodium and sumatriptan succinate. The in vitro dissolution profiles were used to assess drug release from the various dosage forms. The dissolution method consisted of the USP Apparatus 1 and quantitative analyses by HPLC. The dissolution method is summarized below:

TABLE 3

Dissolution Methods

| | |
|---|---|
| Apparatus | USP Type I Rotating Baskets |
| Stirring Speed | 50 rpm |
| Temperature | 37° C. +/− 0.5° C. |
| Filters | 10 μm in-line filters |
| Sample Size | 1 tablet |
| Medium | 900 mL 0.1 M Sodium Phosphate Buffer (pH 7.4) |
| Sampling Times | 15, 30, 45, 60 minutes |

The stability profile of these dosage forms was evaluated using the methods described below. Tablets were packaged into high-density polyethylene (HDPE) bottles in counts of 21 tablets. The HDPE bottles were stored in stability chambers at 25° C./60% RH (closed); 40° C./75% RH (closed), and 40° C./75% RH (open).

The dosage forms were analyzed by conventional wet chemistry methods as described by the USP/NF (U.S.P. Convention In *The United States Pharmacopoeia 23/The National Formulary* 18, The U.S.P. Convention, Inc.: Rockville, Md., 1995; CDER, FDA Guidelines for Dissolution Testing of Immediate Release Oral Dosage Forms, 1997). These methods should be familiar to one skilled in the art of pharmaceutical sciences and include high performance liquid chromatography (HPLC) for assay and dissolution. Samples were taken at different time intervals and analyzed for degradation products by HPLC using a system that may be equipped with an automatic sampler, heated column compartment, gradient elution pump, and variable wavelength UV detector for tablet analyses. The chromatographic conditions for analyses of sumatriptan succinate and naproxen sodium are summarized below.

TABLE 4

Naproxen Sodium Chromatographic Method

| | |
|---|---|
| Column | 4.6-mm × 15-cm column that contains 5-μm packing L1 |
| Mobile Phase | acetonitrile: water: glacial acetic acid (50:49:1) |
| Flow Rate | 1.2 mL/minute |
| Temperature | Ambient |
| Injection Volume | 20 μL |
| Sample | 25 μg/mL in mobile phase |
| Detection | UV @ 254 nm |
| Retention Time | ~30 minutes |

TABLE 5

Sumatriptan Succinate Chromatographic Method

| | |
|---|---|
| Column | 3.9 mm × 15-cm Waters Symmetry C18 |
| Mobile Phase | Acetonitrile: 0.05 M sodium phosphate pH 6.0 (5:95 v/v) |
| Flow Rate | 0.8 mL/minute |
| Temperature | 40° C. |
| Injection Volume | 10 μL |
| Sample | 0.01 mg/mL in mobile phase |
| Detection | UV @ 228 nm |
| Retention Time | ~15 minutes |

C. Results (Comparison of Dosage Forms)

The utility of the invention is demonstrated by the favorable dissolution profile, improved stability, and dosing flexibility for the bilayer tablets compared to alternate dosage forms. The results below were obtained using sumatriptan succinate at 35 mg free base equivalent and naproxen sodium at 375 mg. The preparations are for illustration and do not necessarily represent optimized formulations or processes.

Tablet Dissolution Characteristics

Bilayer tablet dosage forms, consisting of separate layers of sumatriptan succinate and naproxen sodium provide for more rapid release of each component than a core tablet consisting of a physical admixture of sumatriptan succinate and naproxen sodium or a naproxen sodium core tablet with sumatriptan succinate in the film-coat. Rapid or immediate release of each component is advantageous for migraine therapy and, in particular, for the relief of pain. Only the bilayer tablet dosage form exhibits immediate release behavior, whereas the release behavior of other dosage forms is retarded.

TABLE 6

Summary of Naproxen Sodium dissolution profiles for different dosage forms (Naproxen Sodium 375 mg/Sumatriptan 35 mg)
Naproxen Sodium Dissolved (%)
Mean ± RSD (n = 3)[a]

| Timepoint | Bilayer Tablet | Sumatriptan in Film-coat | Physical Admixture |
|---|---|---|---|
| 5 min. | 11.4 ± 5.3 | 0.0 ± N/A | N/A |
| 10 min. | 29.7 ± 2.1 | 3.1 ± 86.7 | N/A |
| 15 min. | 43.7 ± 3.5 | 16.4 ± 6.3 | 26.1 ± 1.7 |
| 30 min. | 78.8 ± 2.9 | 63.0 ± 5.2 | 47.6 ± 3.1 |
| 45 min. | 98.4 ± 1.6 | 89.4 ± 2.3 | 66.8 ± 3.7 |
| 60 min. | 102.2 ± 0.5 | 97.3 ± 0.6 | 82.0 ± 3.0 |
| 90 min. | N/A | N/A | 99.5 ± 1.7 |

[a]Dissolution method [USP Apparatus 1 (50 rpm); phosphate buffer (pH 7.4)] is described elsewhere.

TABLE 7

Summary of Sumatriptan dissolution profiles for different dosage forms (Naproxen Sodium 375 mg/Sumatriptan 35 mg)
Sumatriptan Dissolved (%)
Mean ± RSD (n = 3)[a]

| Timepoint | Bilayer Tablet | Sumatriptan in Film-coat[b] | Physical Admixture |
|---|---|---|---|
| 5 min. | 91.5 ± 7.5 | 54.7 ± 4.0 | N/A |
| 10 min. | 98.4 ± 3.4 | 83.8 ± 2.3 | N/A |
| 15 min. | 99.5 ± 3.2 | 90.9 ± 2.8 | 21.3 ± 4.6 |
| 30 min. | 98.8 ± 3.7 | 95.3 ± 2.4 | 42.6 ± 5.3 |
| 45 min. | 99.1 ± 3.8 | 96.8 ± 1.8 | 62.5 ± 5.4 |
| 60 min. | 98.6 ± 3.7 | 97.5 ± 2.3 | 79.0 ± 3.1 |
| 90 min. | N/A | N/A | 97.7 ± 3.6 |

[a]Dissolution method (USP Apparatus 1 (50 rpm); phosphate buffer (pH 7.4)) is described elsewhere.
[b]Normalized assay values Effect of Storage on Dissolution Characteristics When exposed to humidified conditions, the bilayer tablet dosage form described above exhibits more consistent dissolution profiles than dosage forms manufactured by alternative processes. Dissolution of naproxen sodium at 45 minutes after 3 months decreases the least for the bilayer tablet dosage form, compared to the sumatriptan in film-coat and physical admixture dosage forms (see Table 8). In addition, dissolution of sumatriptan succinate in the physical admixture dosage form decreases significantly, while the bilayer tablet and Sumatriptan in film-coat exhibit no change in release properties (Table 9). Thus, as demonstrated by the dissolution profiles, the bilayer tablet dosage form is more robust and exhibits a superior stability profile than the alternate dosage forms.

TABLE 8

Summary of dissolution profiles after 3 months at 40° C./75% RH (Open) for various dosage forms (Naproxen Sodium 375 mg/Sumatriptan 35 mg) Naproxen Sodium (%)

| Timepoint | | Bilayer Tablet | Sumatriptan in Film-coat | Physical Admixture |
|---|---|---|---|---|
| Time zero | 15 min. | 43.7 | 16.4 | 26.1 |
| | 30 min. | 78.8 | 63.0 | 47.6 |
| | 45 min. | 98.4 | 89.4 | 66.8 |
| | 60 min. | 102.2 | 97.3 | 82.0 |
| 1 month | 15 min. | 30.0 | 2.2 | 19.0 |
| | 30 min. | 58.6 | 33.4 | 31.5 |
| | 45 min. | 79.9 | 61.8 | 44.5 |
| | 60 min. | 95.3 | 82.4 | 56.2 |
| 2 months | 15 min. | 27.7 | 1.9 | 16.5 |
| | 30 min. | 52.8 | 18.6 | 26.8 |
| | 45 min. | 73.2 | 42.9 | 36.2 |
| | 60 min. | 87.5 | 60.0 | 45.9 |
| 3 months | 15 min. | 23.5 | 1.9 | 16.3 |
| | 30 min. | 44.1 | 12.4 | 26.5 |
| | 45 min. | 60.1 | 29.8 | 36.3 |
| | 60 min. | 73.6 | 41.1 | 44.9 |

TABLE 9

Summary of dissolution profiles after 3 months at 40° C./75% RH (Open) for various dosage forms (Naproxen Sodium 375 mg/Sumatriptan 35 mg) Sumatriptan (%)

| Timepoint | | Bilayer Tablet | Sumatriptan in Filmcoat | Physical Admixture |
|---|---|---|---|---|
| Time zero | 15 min. | 99.5 | 75.9 | 21.3 |
| | 30 min. | 98.8 | 80.3 | 42.6 |
| | 45 min. | 99.1 | 81.8 | 62.5 |
| | 60 min. | 98.6 | 82.5 | 79.0 |
| 1 month | 15 min. | 91.2 | 68.2 | 13.3 |
| | 30 min. | 96.2 | 82.5 | 24.7 |
| | 45 min. | 97.3 | 84.4 | 37.5 |
| | 60 min. | 97.7 | 84.9 | 49.6 |
| 2 months | 15 min. | 93.1 | 63.7 | 11.4 |
| | 30 min. | 97.8 | 77.2 | 21.4 |
| | 45 min. | 98.6 | 82.5 | 30.5 |
| | 60 min. | 99.0 | 83.8 | 39.7 |
| 3 months | 15 min. | 92.7 | 62.4 | 11.4 |
| | 30 min. | 96.6 | 75.3 | 20.9 |
| | 45 min. | 97.8 | 81.0 | 30.5 |
| | 60 min. | 97.8 | 82.4 | 39.1 |

Tablet Stability

When exposed to humidified conditions, the bilayer tablet dosage form described above exhibits a more favorable degradation profile, compared to dosage forms manufactured by an alternate process (i.e., physical admixture dosage form). After 3 months storage, naproxen sodium total related substances increased the most for the physical admixture dosage form, compared to the bilayer tablet and the sumatriptan succinate in film-coat dosage forms. Thus, as demonstrated by the naproxen sodium degradation profiles, the bilayer tablet dosage form exhibits a superior stability profile than the alternate dosage forms.

TABLE 10

Summary of related substance results after 3 months for various dosage forms (Naproxen Sodium 375 mg/Sumatriptan 35 mg)

| | Timepoint | Bilayer Tablet | Sumatriptan in Film-coat | Physical Admixture |
|---|---|---|---|---|
| Naproxen Sodium-Total Related Substances (% area) | | | | |
| | Time zero | 0.00 | 0.00 | 0.00 |
| 25° C./60% RH | 1 month | 0.03 | 0.01 | 0.01 |
| | 2 month | 0.02 | 0.02 | 0.01 |
| | 3 month | 0.02 | 0.02 | 0.01 |
| 40° C./75% RH (Closed) | 1 month | 0.01 | 0.03 | 0.01 |
| | 3 month | 0.03 | 0.03 | 0.03 |
| 40° C./75% RH (Open) | 1 month | 0.04 | 0.05 | 0.08 |
| | 2 month | 0.05 | 0.08 | 0.15 |
| | 3 month | 0.07 | 0.10 | 0.23 |
| Sumatriptan-Total Related Substances (% area) | | | | |
| | Time zero | 0.40 | 0.45 | 0.41 |
| 25° C./60% RH | 1 month | 0.18 | 0.20 | 0.18 |
| | 2 month | 0.31 | 0.34 | 0.29 |
| | 3 month | 0.28 | 0.30 | 0.28 |
| 40° C./75% RH (Closed) | 1 month | 0.18 | 0.20 | 0.18 |
| | 3 month | 0.28 | 0.31 | 0.27 |
| 40° C./75% RH (Open) | 1 month | 0.19 | 0.21 | 0.19 |
| | 2 month | 0.28 | 0.34 | 0.31 |
| | 3 month | 0.29 | 0.32 | 0.34 |

Example 3

Pharmacokinetic Characteristics

A. Bioanalytical Methods

A comparative bioavailability study in beagle dogs was performed on ten female animals. Clinical observations included body weights and animal's appearance and behavior immediately before and after dosing and at 2, 8, and 24 hours post-dose. A two-week washout period was included in between administration of each test article. Following oral administration of the test articles (e.g., dosage forms), plasma samples were obtained at specified time intervals over a 48 hour period. Plasma samples were stored in a 20° C. freezer until analyses. The samples were analyzed using an LC/MS/MS assay method summarized below.

TABLE 11

Assay Parameters

Chromatographic Method

| | |
|---|---|
| Column | Extended 150 × 2.1 mm Zorbax C18 |
| Mobile Phase | A: $H_2O$:Formic Acid (100:0.1 v/v) |
| | B: Acetonitrile:Formic Acid (100:0.1 v/v) |
| Program | Gradient |
| Flow Rate | ~250 µL/minute |
| Injection Volume | 3 µL |

Mass Spectrometer Settings

| | |
|---|---|
| Mass Spectrometer | Triple Quadrupole MS |
| Source Temperature | 150° C. |

B. Results

The bilayer tablet dosage form described above (naproxen sodium 375 mg, sumatriptan 35 mg) was found to give a superior pharmacokinetic (PK) profile in beagle dogs compared to dosage forms manufactured by alternate processes. The $T_{max}$ for sumatriptan (mean±sd (n=10)) in a bilayer tablet was found to be 0.50 hr±0.20. In comparison, tablets with sumatriptan in a film coat had a Tmax for sumatriptan of 0.70 hr±0.26 and tablets having an admixture of sumatriptan and naproxen had a $T_{max}$ for sumatriptan of 1.05 hr±0.55. Analysis of these results indicated that the lower $T_{max}$ for the bilayer tablet dosage compared to the admixture was statistically significant (p=0.003, analyzed by Analysis of Variance). A lower $T_{max}$ is advantageous for migraine therapy/pain relief. Thus, as demonstrated by the sumatriptan succinate PK parameters, the bilayer tablet dosage form possesses favorable biopharmaceutic properties compared to the other dosage forms tested.

Example 4

Effect of Dose on Drug Dissolution for Admixed Formulations

The bilayer tablet dosage form provides flexibility in the dose ratios of the components compared to the physical admixture dosage form in which dissolution of both components, naproxen sodium and sumatriptan succinate, decreases with increases in sumatriptan succinate drug loading in the core tablet. The decrease in dissolution is inversely related to the surface area of the tablet. Due to the physical separation of each component in the bilayer tablet dosage form, the release properties are independent of sumatriptan succinate dose. Thus, dose ratios of the components for the bilayer tablet dosage form may be varied within the therapeutic ranges without impacting the release properties.

TABLE 12

Summary of dissolution profiles for physical admixture tablet formulations of varying sumatriptan succinate dose ratios

| Timepoint | Naproxen Sodium 375 mg/ Sumatriptan 25 mg | Naproxen Sodium 375 mg/ Sumatriptan 35 mg | Naproxen Sodium 375 mg/ Sumatriptan 50 mg |
|---|---|---|---|
| | Naproxen Sodium (%) | | |
| 15 min. | 33.6 | 26.1 | 19.7 |
| 30 min. | 60.0 | 47.6 | 36.4 |
| 45 min. | 80.5 | 66.8 | 52.7 |
| 60 min. | 93.2 | 82.0 | 67.0 |
| | Sumatriptan (%) | | |
| 15 min. | 29.9 | 21.3 | 16.6 |
| 30 min. | 56.7 | 42.6 | 32.4 |
| 45 min. | 77.5 | 62.5 | 47.8 |
| 60 min. | 93.2 | 79.0 | 62.9 |

Example 5

Large Scale Manufacturing of Bilayer Tablets

A. Preparation of Granulations

The separate granulations for bilayer tablet dosage forms may be manufactured by various processes depending upon scale and available equipment. The formulations may be easily adapted for a fluid bed granulation process. One suitable method of manufacture is described below.

The intra-granular ingredients described above are separately charged into a fluid bed granulator (Niro, Model MP 2/3) and the materials are fluidized to achieve a uniform distribution of active ingredient. Using a top-spray nozzle, granulating solution, consisting of purified water, USP and povidone, USP, (or other suitable binders) is dispersed at a controlled rate over the fluidized powder bed. Fluid bed granulation is continued until the proper granulation endpoint is reached. After recording the final granulating parameters and amount of solution added, drying is initiated to achieve a loss of 1-5%. The following drying parameters may be used, including an inlet air temperature of 25 to 60° C. and an outlet air temperature of 35 to 55° C. The dried granulation is milled using a Quadro Comil (Model 196) fitted with a suitable screen. The process may be repeated to yield sub-batches that are later combined to provide the desired quantities of each component granulation. Subsequent processing of fluid bed-granulated naproxen sodium and sumatriptan succinate granulations may be carried out as described in subsections B and C below.

B. Pilot-Scale Bilayer Tablet Manufacturing

The formulation and process for making bilayer tablets may be scaled-up for pilot-scale manufacturing (Batch size~125,000 tablets) as described below.

The respective intra-granular ingredients are separately charged into high shear mixer/granulators (Fielder, PMA-65 or PMA-300) and mixed for 5 minutes using a high impeller speed and a high chopper speed setting. Using a spray nozzle, spray purified water, USP, granulating solution, at a suitable rate while mixing continuously at the same mixing conditions. Continue to mix under the same conditions for 1 to 3 minutes or until proper granulation endpoint is reached. Record the final granulating time (solution addition and post-solution addition), amount of solution added, and mixer power consumption readings. Remove the wet granules from the high shear mixer/granulator and place in a drying bowl and dry in a suitable fluid bed dryer (Glatt, Model GPCG 30), to achieve a loss on drying of 1-5%. The following drying parameters may be used, including an inlet air temperature of 25 to 60° C. and an outlet air temperature of 35 to 55° C. The dried granulation is milled using a Quadro Comil (Model 196) fitted with a suitable screen. The process may be repeated to yield sub-batches that are later combined to provide the desired quantities of each component granulation.

The milled granulations are transferred to suitable V-blenders (Patterson-Kelly, 2 or 5 cu. ft.) and mixed for approximately ten minutes with the respective extra-granular ingredients. Pre-sifted lubricants are added and blended for five minutes. Transfer the separate final blends into the hopper(s) for a 35-station, rotary bilayer tablet press (Manesty, Model BB-4). Compress the respective granulations as bilayer tablets using oval-shaped, concave tooling. The naproxen sodium layer is loaded into the die cavity first, and minimal compression force (~500 lbs) is applied to remove entrapped air and form a loose compact. Once acceptable tablet weights are obtained for the naproxen sodium layer, the second layer, consisting of sumatriptan succinate granulation, is loaded into the die cavity. Sufficient compression force (~3,800 lbs) is then applied to yield acceptable bilayer tablets with desired mechanical properties. A tablet hardness of 16 to 18 kp and friability of less than 1% are targeted. In-process controls to ensure acceptable bilayer dosage form include respective weights of each layer, hardness, thickness, friability, and disintegration.

The core bilayer tablets are film-coated in a perforated pan-coater (36" Accela-Cota), using a pre-mixed hydroxypropyl methylcellulose (HPMC) polymer-based dispersion with colorants (Opadry®, Colorcon, Inc.). A 12% w/w aqueous coating suspension is typically prepared. The tablets are coated using two spray guns with an inlet temperature of ~60° C. and an outlet temperature of ~40° C. The pan speed may range from 6 to 12 rpm. The finished tablets are stored in double-lined polyethylene bags prior to packaging.

C. Commercial-Scale Bilayer Tablet Manufacturing

The formulation and process may also be successfully scaled-up for commercial-scale manufacturing (Batch size~1,250,000 tablets). The respective intra-granular ingredients are separately charged into high shear mixer/granulators (Fielder, PMA 300 or PMA-1200). Dry mix for 5 minutes using a high impeller speed and a high chopper speed setting. Using a spray nozzle, spray purified water, USP, granulating solution, at a suitable rate while mixing continuously at the same mixing conditions. Continue to mix under the same conditions for 1 to 3 minutes or until proper granulation endpoint is reached. Record the final granulating time (solution addition and post-solution addition), amount of solution added, and mixer power consumption readings. Remove the wet granules from the high shear mixer/granulator and place in a drying bowl and dry in a suitable fluid bed dryer (Niro Aeromatic, Model T9), to achieve a loss on drying of 1-5%. The following drying parameters may be used, including an inlet air temperature of 25 to 60° C. and an outlet air temperature of 35 to 55° C. The dried granulation is milled using a Quadro Comil (Model 199) fitted with a suitable screen. The process may be repeated to yield sub-batches that are later combined to provide the desired quantities of each component granulation.

The milled granulations are transferred to suitable bin blenders (Bohle Bin Blender) and mixed for approximately ten minutes with the respective extra-granular ingredients, described elsewhere. Pre-sifted lubricants are added and blended for five minutes. Transfer the separate final blends into the hopper(s) for a 51-station, rotary bilayer tablet press (Elizabeth Hata, Model HT-HX51). Compress the respective granulations as bilayer tablets using appropriately shaped tooling. The naproxen sodium layer is loaded into the die cavity first, and minimal compression force (~500 lbs) is applied to remove entrapped air and form a loose compact. Once acceptable tablet weights are obtained for the naproxen sodium layer, the second layer, consisting of sumatriptan succinate granulation, is loaded into the die cavity. Sufficient compression force (~3,800 lbs) is then applied to yield acceptable bilayer tablets with desired mechanical properties. The rotary tablet press speed is approximately 40 rpm. A tablet hardness of 16 to 18 kp and friability of less than 1% are targeted. In-process controls to ensure acceptable bilayer dosage form include respective weights of each layer, hardness, thickness, friability, and disintegration.

The core bilayer tablets are film-coated in a perforated pan-coater (48" Accela-Cota), using a pre-mixed hydroxypropyl methylcellulose (HPMC) polymer-based dispersion with colorants (Opadry®, Colorcon, Inc.). The batch is sub-divided to yield suitable pan loading. A 12% w/w aqueous suspension is typically prepared for coating. The tablets are coated using three spray guns with an inlet temperature of ~60° C. and an outlet temperature of ~40° C. The pan speed may range from 4 to 8 rpm. The finished tablets are stored in double-lined polyethylene bags prior to packaging.

Example 6

Alternate Dosage Ratio Compositions

A. Alternative 1

The respective naproxen sodium and sumatriptan succinate formulations in Example 1 may be easily adapted to provide varying dosages of each component as bilayer tablet dosage forms. The respective mass of each layer of a bilayer tablet is adjusted as weight multiples or factors to achieve alternate dosage ratios within therapeutic ranges. A specific example of a bilayer tablet formulation containing sumatriptan 85 mg and naproxen sodium 500 mg is provided in the tables below.

TABLE 13

Formulation composition for Sumatriptan 85 mg granulation[1]

| Ingredient | mg/Tablet |
|---|---|
| Intra-Granular Ingredients: | |
| Sumatriptan Succinate | 119.00 |
| Lactose Monohydrate, NF | 119.00 |
| Anhydrous Lactose, NF | 238.00 |
| Purified Water, USP[2] | QS |
| Extra-Granular Ingredients: | |
| Anhydrous Lactose, NF | 238.00 |
| Microcrystalline Cellulose, NF | 26.35 |
| Croscarmellose Sodium, NF | 5.10 |
| Magnesium Stearate, NF | 2.55 |
| Total | 510.00 |

[1]Free base equivalent. Representative formulation shown above; quantities of excipients may be varied by ±10% to improve pharmaceutical processing efficiencies.
[2]Purified Water, USP is removed during the drying process.

TABLE 14

Formulation composition for Naproxen Sodium 500 mg granulation[1]

| Ingredient | mg/Tablet |
|---|---|
| Intra-Granular Ingredients: | |
| Naproxen Sodium, USP | 500.00 |
| Microcrystalline Cellulose, NF | 52.95 |
| Povidone, USP | 23.60 |
| Purified Water, USP[2] | QS |
| Extra-Granular Ingredients: | |
| Microcrystalline Cellulose, NF | 52.95 |
| Croscarmellose Sodium, NF | 13.50 |
| Talc, USP | 27.00 |
| Magnesium Stearate, NF | 5.00 |
| Total | 675.00 |

[1]Representative formulation shown above; quantities of excipients may be varied by ±10% to improve pharmaceutical processing efficiencies. Tablet weight may be adjusted for granulation moisture content.
[2]Purified Water, USP is removed during the drying process.

B. Alternative 2

As indicated in Example 6, the respective mass of each layer of a bilayer tablet may 10 be adjusted to achieve alternate dosage ratios within therapeutic ranges. The formulations in Examples 1 and 6 may be modified to increase drug loading and/or improve processing. A specific example of an alternate bilayer tablet formulation containing sumatriptan 40 mg and naproxen sodium 400 mg is provided in the tables below.

TABLE 15

Formulation composition for Sumatriptan 40 mg granulation[1]

| Ingredient | mg/Tablet |
|---|---|
| Intra-Granular Ingredients: | |
| Sumatriptan Succinate | 56.00 |
| Lactose Monohydrate, NF | 56.00 |
| Microcrystalline Cellulose, NF | 13.76 |
| Purified Water, USP[2] | QS |
| Extra-Granular Ingredients: | |
| Microcrystalline Cellulose, NF | 13.76 |
| Croscarmellose Sodium, NF | 1.42 |
| Magnesium Stearate, NF | 1.07 |
| Total | 142.01 |

[1]Free base equivalent. Representative formulation shown above; quantities of excipients may be varied by ±10% to improve pharmaceutical processing efficiencies. A suitable binder may be included depending upon manufacturing process and scale.
[2]Purified Water, USP is removed during the drying process.

TABLE 16

Formulation composition for Naproxen Sodium 400 mg granulation[1]

| Ingredient | mg/Tablet |
|---|---|
| Intra-Granular Ingredients: | |
| Naproxen Sodium, USP | 400.00 |
| Microcrystalline Cellulose, NF | 42.36 |
| Povidone, USP | 18.88 |
| Purified Water, USP[2] | QS |

TABLE 16-continued

Formulation composition for Naproxen Sodium 400 mg granulation[1]

| Ingredient | mg/Tablet |
|---|---|
| Extra-Granular Ingredients: | |
| Microcrystalline Cellulose, NF | 42.36 |
| Croscarmellose Sodium, NF | 10.80 |
| Talc, USP | 21.60 |
| Magnesium Stearate, NF | 4.00 |
| Total | 540.00 |

[1]Representative formulation shown above; quantities of excipients may be varied by ±10% to improve pharmaceutical processing efficiencies. Tablet weight may be adjusted for granulation moisture content.
[2]Purified Water, USP is removed during the drying process.

The formulations in subsections A and B above may be manufactured by processes previously described in Example 5.

All references cited herein are fully incorporated by reference. Having now fully described the invention, it will be understood by one of ordinary skill in the art that the invention may be performed within a wide and equivalent range of conditions, parameters and the like, without affecting the spirit or scope of the invention or any embodiment thereof.

What is claimed is:

1. A multilayer pharmaceutical tablet comprising naproxen and a triptan and, wherein:
   a) substantially all of said triptan is in a first layer of said tablet and substantially all of said naproxen is in a second, separate layer; and
   b) said first layer and said second layer are in a side by side arrangement such that the dissolution of said naproxen occurs independently of said triptan.

2. The tablet of claim 1, wherein said naproxen is in the form of naproxen sodium at between 200 and 600 mg.

3. The tablet of claim 1, wherein said triptan is selected from the group consisting of: sumatriptan, eletriptan, rizatriptan, frovatriptan, alniotriptan, zolniitriptan, and naratriptan.

4. The tablet of claim 1, wherein said triptan is sumatriptan.

5. The tablet of claim 4, wherein said sumatriptan is in the form of sumatriptan succinate at between 25 and 100 mg.

6. The tablet of claim 1, wherein said first layer and said second layer are juxtaposed symmetrically along a single planar surface such that essentially all of said first layer is on one side of said planar surface and essentially all of said second layer is on the other side of said planar surface.

7. The tablet of claim 6, wherein said first layer and said second layer contact one another along said single planar surface.

8. The tablet of claim 6, wherein said first layer and said second layer are separated by at least one additional layer.

9. The tablet of any one of claims 1-8, wherein said tablet is a bilayer dosage form.

10. The tablet of any one of claims 1-8, further comprising a coating layer surrounding both said first layer and said second layer.

11. The tablet of any one of claims 2, 3 or 6-8, wherein said triptan is sumatriptan.

12. The tablet of claim 11, wherein said sumatriptan is in the form of sumatriptan succinate at between 25 and 100 mg.

13. A method of treating a patient for headache, comprising administering to said patient the tablet of any one of claims 1-8, wherein said patient is treated at a dosage effective to alleviate the pain associated with said headache.

14. The method of claim 13, wherein said headache is migraine headache.

15. A method of treating a patient for headache, comprising administering to said patient the tablet of claim 9, wherein said patient is treated at a dosage effective to alleviate the pain associated with said headache.

16. The method of claim 15, wherein said headache is migraine headache.

17. A method of treating a patient for headache, comprising administering to said patient the tablet of claim 10, wherein said patient is treated at a dosage effective to alleviate the pain associated with said headache.

18. The method of claim 17, wherein said headache is migraine headache.

19. A multilayer pharmaceutical tablet comprising an NSALD and a triptan, wherein
  a) substantially all of said triptan is in a first layer of said tablet and substantially all of said NSALD is in a second, separate layer; and
  b) said first layer and said second layer are in a side by side arrangement such that the dissolution of said NSAID occurs independently of said triptan.

20. A method for rapid release of sumatriptan and naproxen from an oral dosage form in a patient, the method comprising administering to said patient the tablet of claim 4 or claim 5, wherein in said patient, dissolution of sumatriptan and naproxen is faster from said tablet as compared to dissolution of sumatriptan and naproxen from a tablet where sumatriptan and naproxen are in a physical admixture.

* * * * *